United States Patent
Cook

(10) Patent No.: US 7,357,845 B2
(45) Date of Patent: *Apr. 15, 2008

(54) METHODS OF MAKING LARYNGEAL MASKS

(75) Inventor: Daniel J. Cook, Richmond Heights, MO (US)

(73) Assignee: Cookgas, L.L.C., St. Louis, MO (US)

( * ) Notice: Subject to any disclaimer, the term of this patent is extended or adjusted under 35 U.S.C. 154(b) by 713 days.

This patent is subject to a terminal disclaimer.

(21) Appl. No.: 10/691,399

(22) Filed: Oct. 22, 2003

(65) Prior Publication Data

US 2005/0016529 A1 Jan. 27, 2005

Related U.S. Application Data

(60) Continuation-in-part of application No. 09/829,157, filed on Apr. 9, 2001, now Pat. No. 6,705,321, which is a continuation-in-part of application No. 09/179,928, filed on Oct. 27, 1998, now Pat. No. 6,422,239, which is a division of application No. 08/843,631, filed on Apr. 10, 1997, now Pat. No. 5,937,860.

(51) Int. Cl.
B32B 37/00 (2006.01)

(52) U.S. Cl. ............ 156/242; 128/207.14; 128/207.15; 264/279

(58) Field of Classification Search ............... 156/73.1, 156/242, 500, 580.1, 580.2; 128/207.14, 128/207.15, 200.26; 264/259, 261, 271.1, 264/275, 279

See application file for complete search history.

(56) References Cited

U.S. PATENT DOCUMENTS

| 3,734,100 A | 5/1973 | Walker et al. |
|---|---|---|
| 4,863,439 A | 9/1989 | Sanderson |
| 4,995,388 A | 2/1991 | Brain |
| 5,024,220 A | 6/1991 | Holmgreen et al. |
| 5,277,178 A | 1/1994 | Dingley |
| 5,282,464 A | 2/1994 | Brain |
| 5,303,697 A | 4/1994 | Brain |
| 5,391,248 A * | 2/1995 | Brain .................. 156/242 |
| 5,392,774 A | 2/1995 | Sato |
| 5,529,582 A | 6/1996 | Fukuhara |
| 5,545,048 A | 8/1996 | Maeda |
| 5,569,222 A | 10/1996 | Haselhorst et al. |
| 5,623,921 A | 4/1997 | Kinsinger et al. |
| 5,632,271 A | 5/1997 | Brain |
| 5,643,174 A | 7/1997 | Yamamoto et al. |
| 5,653,231 A | 8/1997 | Bell |
| 5,682,880 A | 11/1997 | Brain |
| 5,713,348 A | 2/1998 | Pell |
| 5,772,643 A | 6/1998 | Howell et al. |
| 5,787,879 A | 8/1998 | Gibson |

(Continued)

Primary Examiner—James Sells
(74) Attorney, Agent, or Firm—Lewis, Rice & Fingersh, L.C.

(57) ABSTRACT

A method of making a laryngeal airway of the type that includes a respiratory tube and an inflatable positioning shield having a base and an inflatable, hollow peripheral portion is described herein. The method includes introducing at least one molding material into a mold, wherein the mold has a cavity defined by internal walls, wherein the internal walls conform to external walls of the laryngeal mask, and wherein the mold has a core within its cavity that is adapted to form the hollow portions of the laryngeal airway.

36 Claims, 8 Drawing Sheets

U.S. PATENT DOCUMENTS

| | | |
|---|---|---|
| 5,878,745 A | 3/1999 | Brain |
| 6,705,318 B1 * | 3/2004 | Brain ................... 128/207.14 |
| 7,096,868 B2 * | 8/2006 | Tateo et al. ............ 128/207.15 |
| 7,097,802 B2 * | 8/2006 | Brain ........................ 264/255 |

* cited by examiner

METHODS OF MAKING LARYNGEAL MASKS

CROSS-REFERENCE TO RELATED APPLICATIONS

This is a continuation-in-part of U.S. patent application Ser. No. 09/829,157, filed Apr. 9, 2001, and issued as U.S. Pat. No. 6,705,321 on Mar. 16, 2004, which is a continuation-in-part of U.S. patent application Ser. No. 09/179,928, filed on Oct. 27, 1998, and issued as U.S. Pat. No. 6,422,239 on Jul. 23, 2002 which is a divisional of Ser. No. 08/843,631, now U.S. Pat. No. 5,937,860, which issued on Apr. 10, 1997.

STATEMENT REGARDING FEDERALLY SPONSORED RESEARCH OR DEVELOPMENT

Not applicable.

BACKGROUND OF THE INVENTION

This invention relates to methods of making artificial airway devices, and more specifically to methods of making artificial airway devices that are designed to facilitate lung ventilation and the insertion of endotracheal tubes or related medical instruments into the laryngeal opening of an unconscious patient.

In general, laryngeal masks allowing for both rapid lung ventilation and the insertion of medical instruments and tubes into the laryngeal openings of patients have been described in patents such as U.S. Pat. No. 5,937,860 to Cook. Consisting of two essential parts, a breathing tube and an inflatable positioning shield or mask, these instruments or devices are inserted blindly into a patient's throat, and when properly positioned, terminate at the laryngeal opening. A seal is then formed around the circumference of the laryngeal opening by the inflation of the ring-like peripheral portion of the mask. Inflation of the peripheral portion exerts pressure against both the front and rear portions of the oropharynx, securing the device in place such that the laryngeal opening is positioned within a recessed cavity in the mask face. Extending from a point external to the oral cavity, the flexible breathing tube terminates within the recessed cavity, aligned axially with the laryngeal opening. The positioning of the flexible breathing tube allows the passage of endotracheal tubes or related medical instruments into the laryngeal opening, in addition to allowing for lung ventilation.

Laryngeal airway devices of this type are typically manufactured by one of two methods. One method involves forming the upper and lower portions of the inflatable peripheral portion of the mask and the base separately using various molding techniques. The two portions are then connected using heat, pressure, adhesive, or combinations of each. Laryngeal airway devices of this type have also been manufactured using blow-molding techniques, which involve forming an essentially flat balloon, and later bringing the central portion of the flat balloon together using heat or pressure to form the inflatable, peripheral portion and the base. The flattened central portion forms the base, while the peripheral portion of the balloon remains hollow. While these methods have been successfully used to manufacture laryngeal airway devices, the parts must be glued together. First, several process steps are necessary to manufacture a market-ready product, which results in increased manufacturing costs. Second, where the components are manufactured separately, and later joined, seams are formed, which provide areas of comprised stability. Third, blow-molding procedures produce walls of uniform thickness, which makes producing airway walls of varying thicknesses impossible.

Therefore, a method for producing laryngeal airway devices of the type that include a respiratory tube and an inflatable positioning shield having a central support structure and an inflatable peripheral portion is needed that avoids these problems.

SUMMARY OF THE INVENTION

Briefly, in a first aspect of the invention, a method of making a laryngeal airway of the type that includes a respiratory tube and an inflatable positioning shield, the shield having a base and a hollow, peripheral portion and the respiratory tube comprising a tubular body, a proximal end lumen, and a distal end lumen formed therethrough is provided that comprises introducing at least one molding material into a mold, wherein the mold has a cavity defined by internal walls, wherein the internal walls conform to external walls of the laryngeal airway, and wherein the mold has at least one core within its cavity, the core being adapted to form the proximal end lumen, tubular body and the distal end lumen of the respiratory tube and the hollow, peripheral portion of the inflatable positioning shield, and allowing the molding material to cure about the internal walls of the mold and the at least one core, thereby forming the laryngeal airway;

In a second aspect of the invention, a method of making a laryngeal airway of the type described above is provided that comprises introducing at least one molding material into a mold, wherein the mold has a cavity defined by the internal walls, wherein the internal walls conform to external walls of the laryngeal airway, and wherein the mold has at least one core within its cavity that is adapted to form the respiratory tube and the hollow, peripheral portion of the positioning shield, wherein the at least one core comprises a proximal portion, central portion and a distal portion, the proximal portion adapted to form the proximal end lumen, the tubular body, and the distal end of the respiratory tube, the central portion being adapted to form the distal lumen of the respiratory tube and the distal portion adapted to form the hollow, peripheral portion of the inflatable positioning shield and allowing the molding material to cure about the internal walls of the mold and the core, thereby forming the laryngeal airway;

In a third aspect of the invention, a method of making a laryngeal airway of the type described above is provided that comprises introducing a molding material polyvinyl chloride or silicone onto internal walls of a mold, wherein the mold has a cavity defined by the internal walls, wherein the internal walls conform to external walls of the inflatable positioning shield, and wherein the mold has at least one core within its cavity that is adapted to form the hollow, peripheral portion of the positioning shield, and allowing the molding material to cure about the internal walls of the mold and the at least one core, thereby forming the laryngeal airway, wherein the at least one core comprises a proximal portion, central portion, and a distal portion, the proximal portion adapted to form the proximal end lumen, the tubular body, and the distal end of the respiratory tube, the central portion adapted to form the distal lumen of the respiratory tube and the distal portion adapted to form the hollow, peripheral portion of the inflatable positioning shield, and allowing the molding material to cure about the internal walls of the mold and the core, thereby forming the laryngeal airway; and In a fourth aspect of the invention, a method of making a laryngeal mask of the type that includes a respiratory tube and an inflatable positioning shield, the shield having a base and a hollow peripheral portion, the respiratory tube comprising a proximal end lumen, a tubular body of sufficient size to permit passage of endotracheal tubes or related medical instruments therethrough, and a distal end secured to the positioning shield, the distal end terminating at a distal lumen, which is secured to the positioning shield is provided that comprises introducing silicone into a mold, wherein the mold has a cavity defined by internal walls, wherein the mold has at least one core within its cavity, the core being adapted to form the respiratory tube and the hollow peripheral portion of the positioning shield, wherein the internal walls of the mold conform to external walls of the laryngeal airway, wherein the at least one core comprises a proximal portion, a central portion, and a distal portion, the proximal portion adapted to form the proximal end lumen, the tubular body, and the distal end of the respiratory tube, the central portion adapted to form the distal end lumen of the respiratory tube and the distal portion adapted to form the hollow peripheral portion of the inflatable positioning shield, and allowing the silicone to cure about the internal walls of the mold and the at least one core, thereby forming the laryngeal airway.

BRIEF DESCRIPTION OF THE DRAWINGS

In the drawings.

Corresponding reference numerals indicate corresponding parts throughout the several figures of the drawings.

DESCRIPTION OF THE PREFERRED EMBODIMENTS

Figure 1:
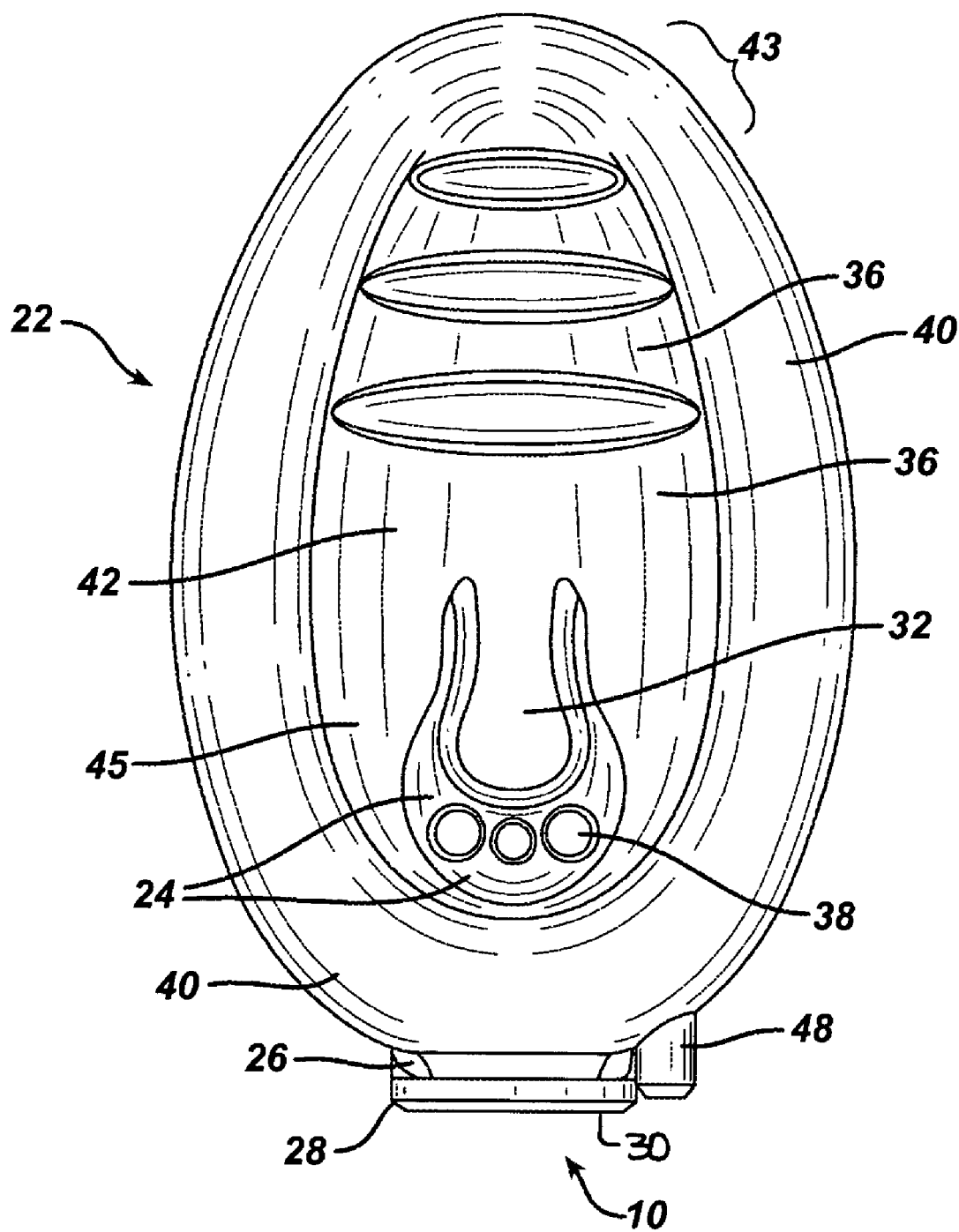
FIG. 1 is a top view of the laryngeal mask illustrating the respiratory tube and the inflatable positioning shield.
Figure 2:
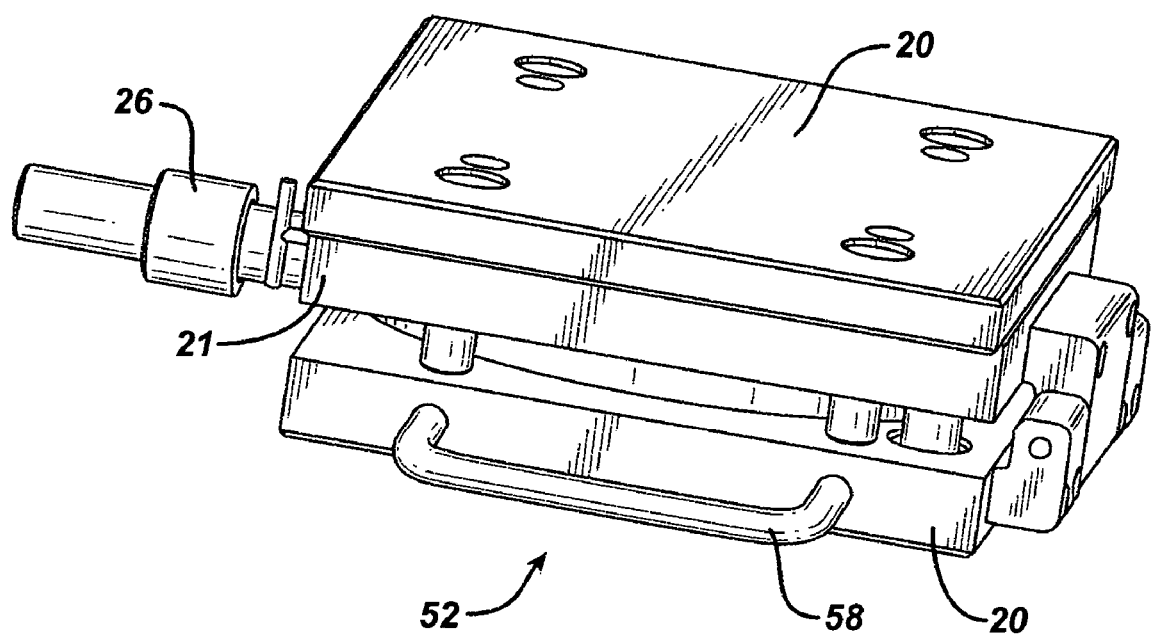
FIG. 2 is a plan view of one embodiment of the mold of the invention.

New and useful methods for making a laryngeal airway of the type that includes a respiratory tube and an inflatable positioning shield having a base and an inflatable, hollow peripheral portion, have been discovered. Referring to FIG. 1, one embodiment the invention is shown in reference to an inflatable positioning shield 22 attached to the distal end of a respiratory tube 26. Laryngeal mask 10 generally comprises a respiratory tube 26 providing ventilation, a direct pathway for medical devices and instruments into the laryngeal inlet, and may also provide alternate airways 38 to prevent blockage of breathing tubes during patient ventilation, and an inflatable positioning shield 22, which will be understood to be relatively shaped for manipulated entry into position within a patient's pharyngeal cavity. Respiratory tube 26 may be of sufficient size to permit proximal end 28 to be accessible for ventilation outside of the patient's mouth. However, respiratory tube 26 may not be of sufficient size to permit proximal end 28 to be accessible to ventilation outside of the mouth. In this embodiment, at least one additional respiratory tube may be connected to proximal end 28 of respiratory tube 26 to extend the length of respiratory tube 26.

Respiratory tube 26 comprises a proximal end 28, a proximal end lumen 30, a tubular body of sufficient size to permit passage of endotracheal tubes or related medical instruments therethrough, and a distal end 24 passing through and secured to positioning shield 22. Distal end 24 of respiratory tube 26 terminates at distal lumen 32, which passes through and is secured to positioning shield 22 such that tubes and instruments passing through respiratory tube 26 will be directed into the laryngeal opening. Inflatable positioning shield 22 generally comprises an inflatable, hollow, peripheral portion 40, which encircles a base 42. A rear portion 45 and a shield recess 36 are generally formed upon inflation of peripheral portion 40 between base 42 and peripheral portion 40.

Figure 3:
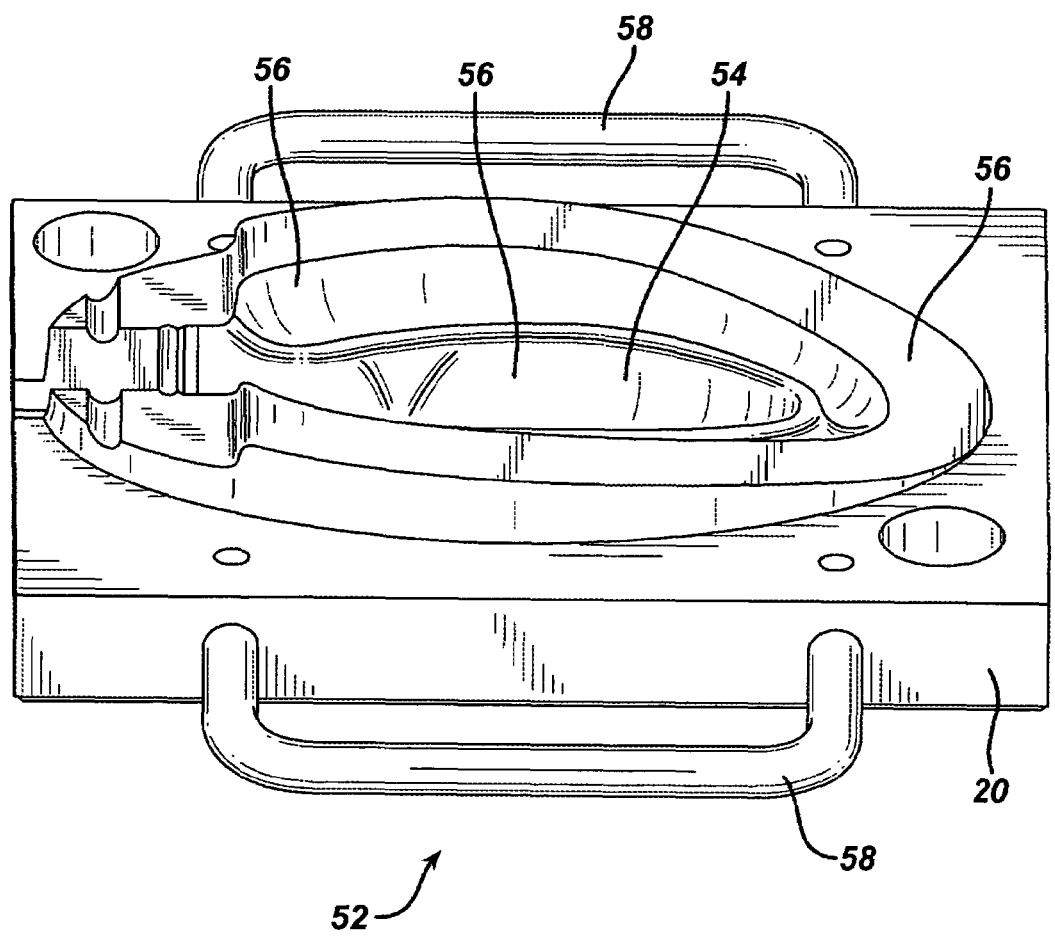
FIG. 3 is a partial plan view of one embodiment of the mold of the invention, illustrating how the internal walls of the mold conform to the external walls of a laryngeal airway device.

It is contemplated that airway devices of the general type described herein may be produced using the methods of the invention. However, as one skilled in the art can appreciate, the methods described herein may be employed to produce various embodiments of laryngeal airway 10. With reference to FIG. 3, the internal walls 56 of mold 52 must conform to the exterior walls of the specific airway device desired. For example, and with reference to FIG. 1, the methods described herein may be employed to produce an embodiment of laryngeal airway 10 wherein base 42 comprises ventilation lumens 38 disposed about distal end 24 of respiratory tube 26. Distal lumen 32 may be of various cross-sectional shapes including, but not limited to a keyhole shape, oval shape, or circular shape. Peripheral portion 40 may comprise a recessed front portion 43, as shown in FIG. 1, and described in U.S. Pat. No. 5,937,860 to Cook. Recessed front portion 43 is adapted to cup a patient's trachea after inflation of peripheral portion 40. Also, respiratory tube 26 may have various cross-sectional shapes including, but not limited to circular and oval shapes. Respiratory tube 26 may also be secured to the proximal end of positioning shield 22 and not pass through, or be secured to positioning shield 22. Further, the laryngeal airway itself may be of various cross-sectional shapes, including but not limited to oval, or wedge shapes. All cross-sectional references referred to herein are perpendicular to the longitudinal axis of the body of the tube, or other component.

In accordance with the invention, and with reference to FIGS. 2-10, one embodiment of the method comprises introducing at least one molding material into mold 52, wherein mold 52 has a cavity 54 defined by internal walls 56, wherein internal walls 56 conform to the laryngeal airway 10, and wherein mold 52 includes at least one core 60 within internal walls 56 that is adapted to form the proximal end lumen 30, tubular body and distal lumen 32 of respiratory tube 26 and hollow peripheral portion 40 of positioning shield 22. The molding material is allowed to cure about internal walls 56 and core 60, thereby forming laryngeal airway 10. Laryngeal airway 10 is then stripped out of mold 52. Core 60 is then removed from mold 52 by pulling it out of proximal end lumen 30. It should be noted that it is within the scope of the invention for the sequence of the steps of the invention to be altered.

Mold 52 is designed to produce a laryngeal airway in a market-ready configuration. The airway produced need not be inverted prior to use as with prior art molding processes. The molded product is stripped from mold 52 and core 60 is removed from the airway formed. This reduces the amount of time and financial resources necessary to manufacture airway 10. The phrase "laryngeal airway" refers to the device generally described and shown at 10 in FIG. 1. However, as used herein, the phrase applies more broadly to the laryngeal mask portion of the laryngeal airway device that includes an inflatable peripheral portion and a base. Accordingly, as used herein, a laryngeal airway may, or may not comprise a respiratory tube.

Figure 5:
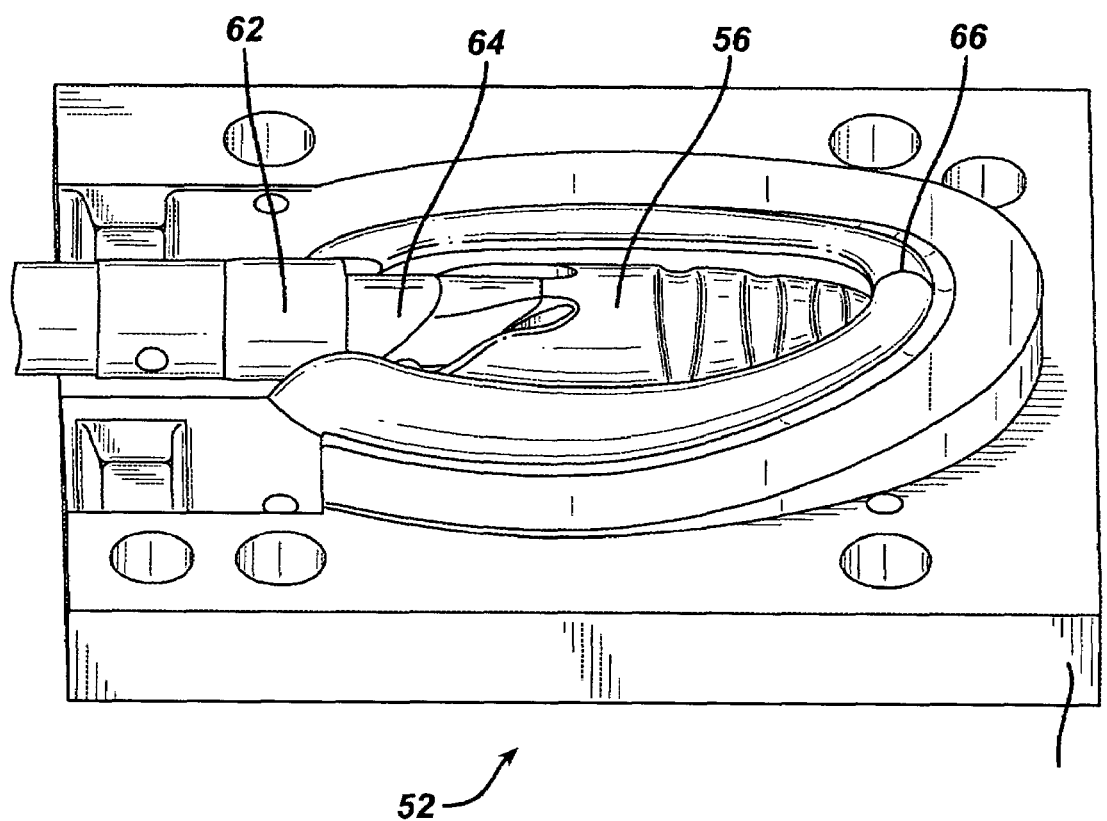
FIG. 5 is a partial plan view of one embodiment of the mold of the invention, illustrating proper placement of the core inside the mold.
Figure 6:
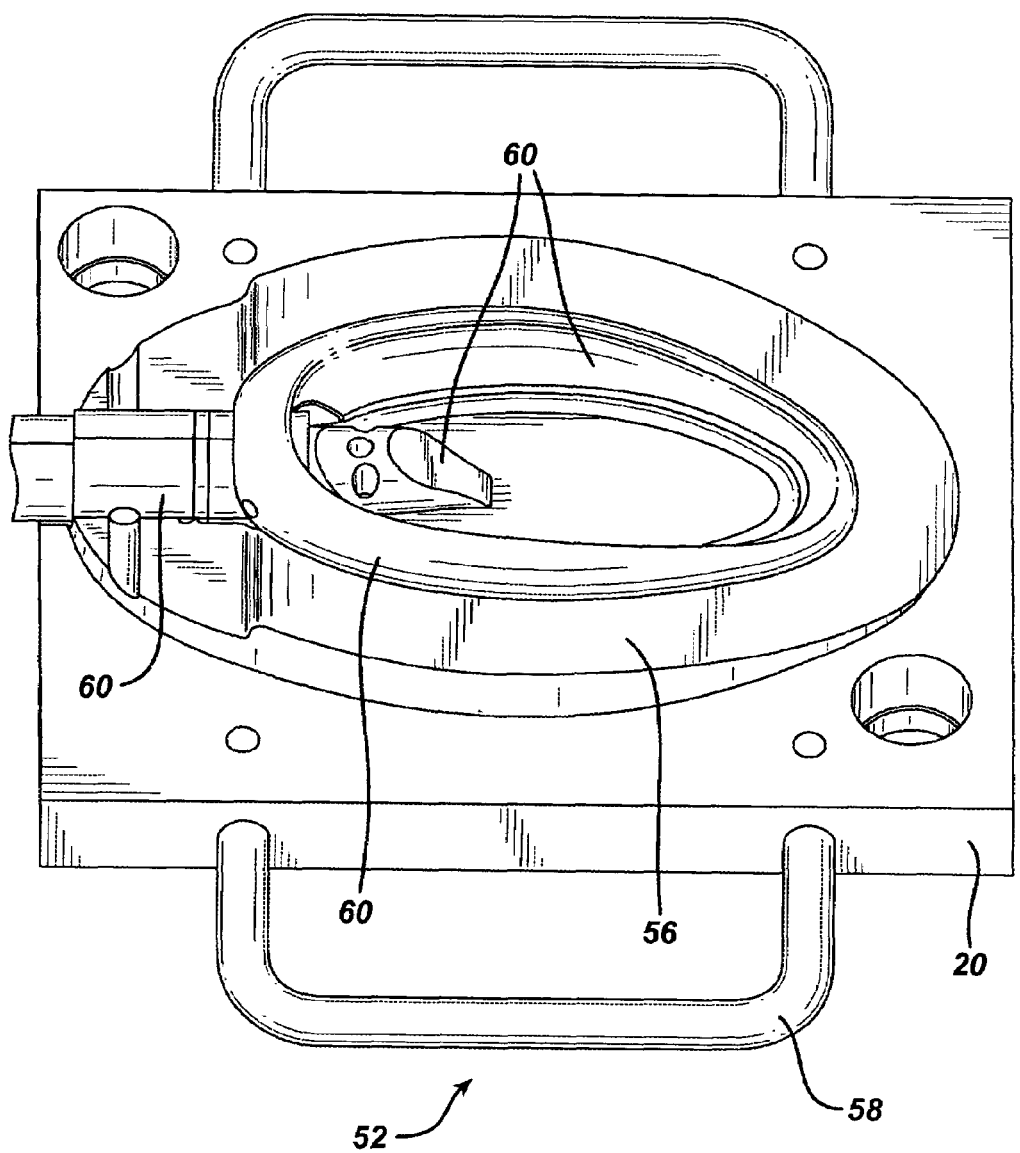
FIG. 6 is a partial plan view of one embodiment of the mold of the invention, illustrating proper placement of the cores inside the mold.
Figure 7:
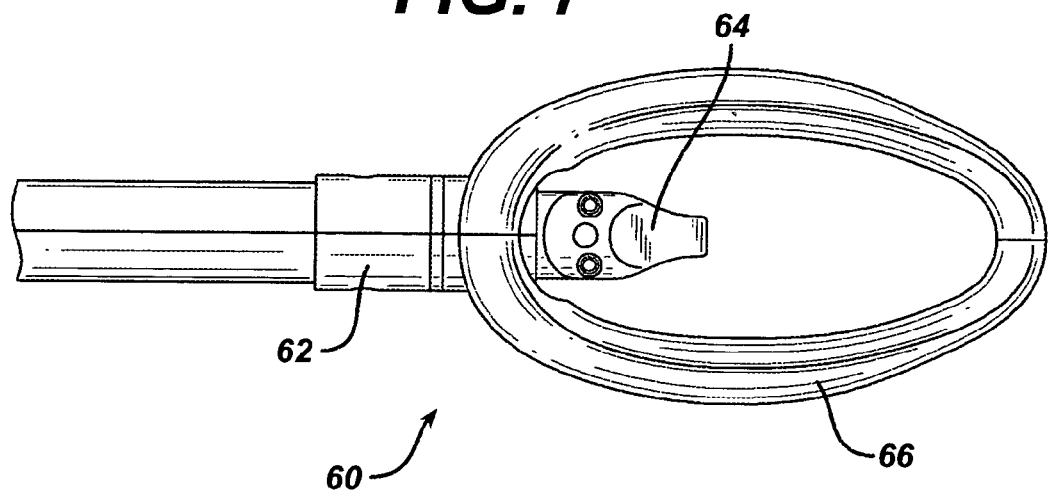
FIG. 7 is a top view of one embodiment the core of the invention.
Figure 8:
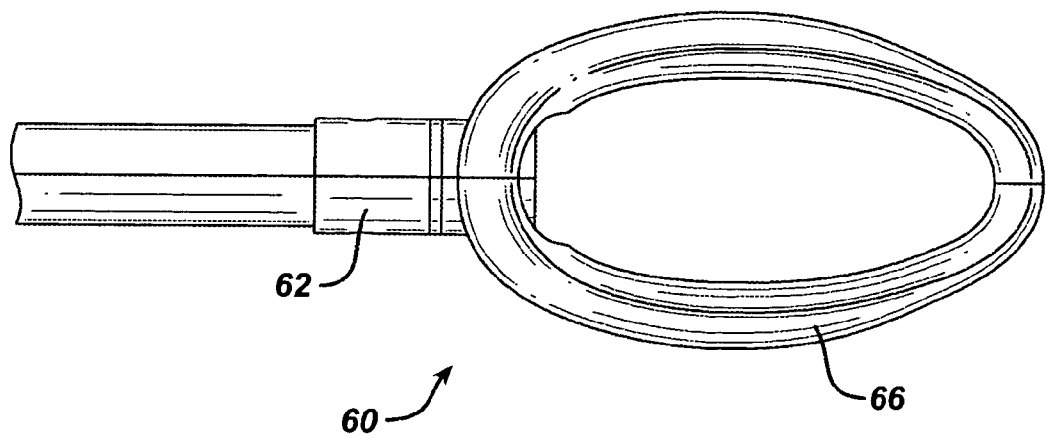
FIG. 8 is a top view of a second embodiment of the core of the invention.
Figure 9:
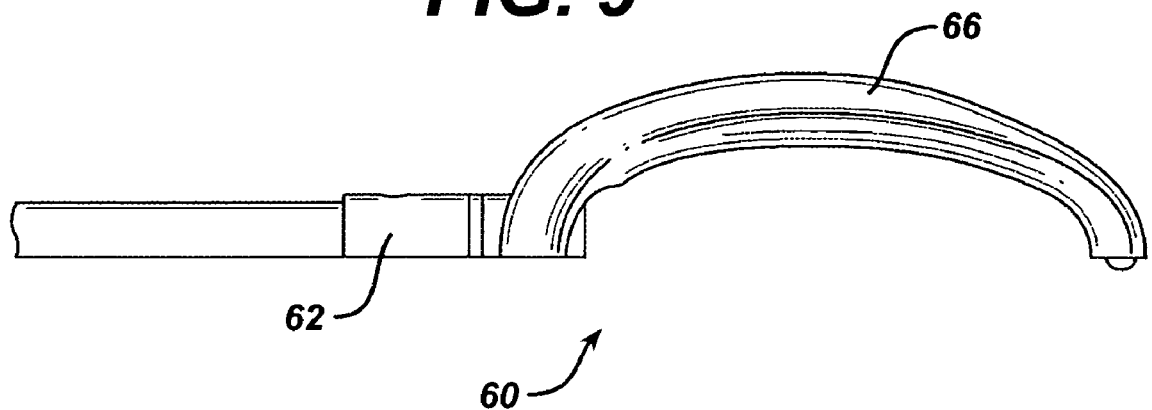
FIG. 9 is a top view of a third embodiment of the core of the invention.
Figure 10:
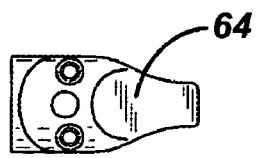
FIG. 10 is a top view of one embodiment of a core of the invention, used to create the respiratory tube and lumens therethrough.

With reference to FIGS. 5-10, at least one core 60 is employed in the methods of the invention to create voids that form hollow peripheral portion 40 and/or respiratory tube 26. Core 60 is generally placed inside mold 52 prior to the introduction of molding material therein, and removed after the molding material has cured. With reference to FIGS. 5 and 6, core 60 is simply placed inside cavity 54. With reference to FIGS. 7-10, core 60 generally includes a proximal portion 62, a central portion 64 and a distal portion 66. It should be noted that in embodiments where respiratory tube 26 does not pass through positioning shield 22, core 60 may not include central portion 64. Proximal portion 62 is adapted to form the proximal end lumen 30, tubular body and distal end 24 of respiratory tube 26. Distal portion 66 is adapted to form hollow peripheral portion 40 of positioning shield 22. In embodiments where respiratory tube 26 passes through positioning shield 22, core 60 includes central portion 64. Central portion 64 is adapted to form distal lumen 32 and the tubular body of respiratory tube 26, which passes through and is secured to positioning shield 22. Central portion 64 is generally connected to distal portion 66 and proximal portion 62 using pins, or any other connection means. Core 60 may include a means for handling to facilitate insertion and removal of core 60. The molding material is introduced onto internal walls 56 of mold 52 by any known means of accomplishing such. A liquid form of the molding material may be poured into mold 52. A paste form of the molding material may be introduced into mold 52 by pouring, pressing, or placing the molding material into mold 52 using pressure. The molding material may also be dripped or sprayed into mold 52. To facilitate distribution of the molding material onto internal walls 56, and in one embodiment of the invention, mold 52 may also be manipulated after introduction of the molding material therein. Mold 52 may also be vibrated, shaken, or rotated to facilitate distribution.

In one embodiment of the invention, mold 52 is warmed before or after the molding material is introduced thereto. As used herein, the term "warm" means being at a temperature higher than room temperature. Accordingly, the term "warming" means to elevate the temperature to a temperature that is higher than room temperature. Generally, some liquid molding materials are warmed prior to introduction into mold 52. Some molding materials are in a liquid state only when warmed and solidify when cooled to room temperature. The temperature necessary to liquefy the molding materials of the invention varies depending on the specific composition of the molding material. Some molding materials require a very high temperature to achieve a liquid state, while others require a lower temperature to achieve a liquid state. It should be understood, however, that it is not critical that the molding materials be liquid to practice the invention. It should also be noted that some molding materials form a paste and not a liquid when warmed. The utilization of these molding materials is also within the scope of the invention.

The molding material is allowed to cure about internal walls 56 and core 60 to form laryngeal airway 10. The curing process generally only takes a few minutes to complete, but may take more or less time depending upon the specific molding material employed, the environmental conditions that exists at the time of curing, and the desired thickness of the laryngeal airway 10. To decrease the curing time, the mold may be cooled or warmed either before the molding material is introduced therein, or after the introduction of the molding material therein, depending on the composition of the molding material employed.

Figure 4:
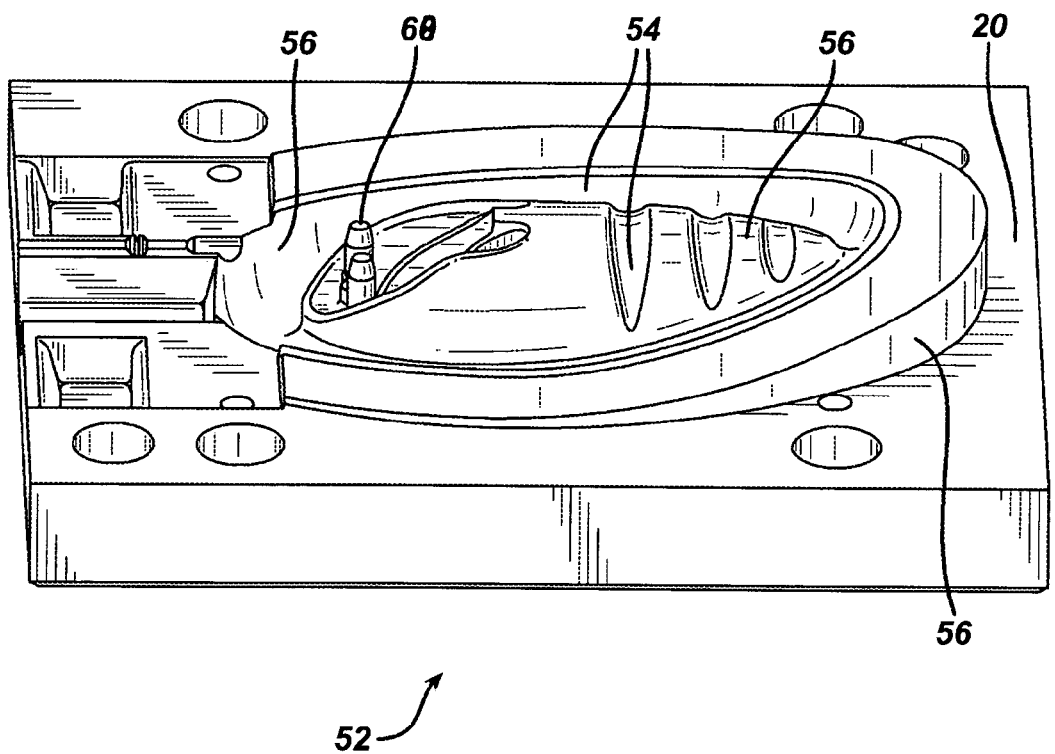
FIG. 4 is a partial plan view of one embodiment of the mold of the invention, illustrating how the internal walls of the mold conform to the external walls of a laryngeal airway device.

The methods of the invention are achieved utilizing a mold that is designed to produce an inflatable peripheral portion of positioning shield 22. With reference to FIGS. 3 and 4, mold 52 has a cavity defined by internal walls 56, which conform to the external surface of hollow peripheral portion 40. Mold 52 conforms to the outer surface of peripheral portion 40, forming the walls of laryngeal airway 10. Mold 52 may be designed to produce only positioning shield 22. Mold 52 may also be designed to produce respiratory tube 26. Respiratory tube 26 may be connected to proximal end 30 of positioning shield 22. Respiratory tube 26 may also pass through and be secured to proximal end 45 of positioning shield 22, as shown in FIG. 1. In embodiments wherein respiratory tube 26 does not pass through positioning shield 22, respiratory tube 26 may be connected, by any known means for accomplishing such, to positioning shield 22. Respiratory tube 26 may be connected to inflatable positioning shield 22 immediately after inflatable positioning shield 22 is formed, or after some time. In embodiments wherein respiratory tube 26 passes through positioning shield 22, a second respiratory tube, or additional tubing may be attached to the proximal or attachment end of respiratory tube 26 to extend the length of respiratory tube 26 to at least a point that is external to the patient's mouth.

The methods described herein may be employed to produce various embodiments of laryngeal airway 10. Internal walls 56 of mold 52 must conform to the exterior walls of the specific airway device desired. For example, and with reference to FIG. 1, mold 52 may be designed in accordance with the invention to produce an embodiment of laryngeal airway 10 wherein base 42 comprises ventilation lumens 38 disposed about distal end 24 of respiratory tube 26. Distal lumen 32 may be of various cross-sectional shapes including, but not limited to a keyhole shape, oval shape, or circular shape. Peripheral portion 40 may comprise a recessed front portion 43, as shown in FIG. 1, and described in U.S. Pat. No. 5,937,860 to Cook. Recessed front portion 43 is adapted to cup a patient's trachea after inflation of the peripheral portion 40. Also, respiratory tube 26 may have various cross-sectional shapes including, but not limited to circular and oval shapes. Further, positioning shield 22 may be of various cross-sectional shapes, including but not limited to oval, or wedge shaped. Molds that are adapted to produce these, and other embodiments of laryngeal airway 10 are within the scope of this invention.

Similarly, molds that are adapted to produce portions of laryngeal airway 10 are within the scope of the invention. Mold 52 simply must conform to the components of the laryngeal airway that are desired. In one embodiment of the invention, mold 52 is designed to produce inflatable positioning shield 22. Respiratory tube 26 is connected thereto after positioning shield 22 is produced.

In one specific embodiment of the invention, the internal walls of mold 52 are designed to produce a laryngeal mask that comprises an inflatable positioning shield and a respiratory tube. The inflatable positioning shield has a hollow peripheral portion in fluid communication with the base, the base has a recessed front portion that is sufficiently pliable to cup a patient's trachea after inflation of the inflatable positioning shield, a shield recess formed after inflation of the peripheral portion, and a rear portion formed between the base and the peripheral portion after inflation of the peripheral portion. The respiratory tube has a proximal end lumen 30, a curved tubular body of sufficient size to permit passage of endo-tracheal tubes or related medical instruments therethrough, and a distal end passing through and secured to the rear portion of the positioning shield, the distal end terminating at a distal lumen, the distal lumen passing through and secured to the rear portion of the positioning shield. In a more specific embodiment, the respiratory tube is flexible.

In accordance with one embodiment of the invention, mold 52 is filled with molding material after insertion of core 60. However, in alternative embodiments of the invention, core 60 may be inserted into mold 52 after it is filled with the molding material. The amount introduced into mold 52 varies and is depended upon various factors, including the specific environmental conditions present at the time of introduction of the molding material into the mold, the specific composition of the molding material employed, as well as the shape, size and configuration of mold 52. It should also be understood that the thickness of the walls is not critical to achieve the objects of the invention. The walls formed, however, must be thick enough to withstand the pressure and wear associated with patient intubation and thin enough such that patient intubation is not inhibited or complicated. When inflated properly, peripheral portion 40 exerts pressure against the structures of the oropharynx to form a substantially airtight seal around the laryngeal opening. One skilled in the art could readily determine the proper amount of molding material that should be introduced into mold 52 without undue experimentation. Generally, and in one embodiment of the invention, the molding material is introduced in an amount that will create external walls of laryngeal airway 10 that are about 0.5 to about 1.5 millimeters thick. If it is found that the walls are too thin after the molding material has cured, an additional amount of the molding material may be introduced to the internal walls of the mold while the cured product remains inside mold 52. This step may be repeated until the desired thickness is achieved.

As one skilled in the art would appreciate, mold 52 may also be designed to produce any component of laryngeal airway 10. As such, the need for connecting other portions of the laryngeal airway 10, such as respiratory tube 26 and base 42 are avoided. The mold simply must conform to the outer surface of the specific embodiment of laryngeal airway 10 desired, including those components to be molded. For example, and in one embodiment, mold 52 is designed to produce base 42, peripheral portion 40, and respiratory tube 26. In that case, the internal walls of the mold conform to the external surface of peripheral portion 40, base 42 and the external surface of respiratory tube 26. In this embodiment, core 60 is employed to produce the hollow portions. In another embodiment of the invention, mold 52 conforms to the external walls of the hollow peripheral portion 40. Base 42 may be manufactured separately and connected to peripheral portion 40 before, or after, the molding material is introduced into mold 52. In embodiments wherein base 42 is connected to peripheral portion 40 before the molding material is allowed to cure, base 42 is generally inserted or placed inside mold 52 before the molding material is introduced. In embodiments wherein base 42 and peripheral portion 40 are connected after the molding material is allowed to cure, the two components are connected by known connection methods, including but not limited to the use of heat, pressure, or adhesives. The specific adhesive used is not critical to the methods of invention and is largely dependant upon the specific composition of the molding material employed. Suitable adhesives can be readily determined without undue experimentation and are widely commercially available.

By way of further example, where small diameter lumens 38 in distal end 24 of respiratory tube 26 are desired, cores or extensions 68 of mold 52 may be employed. Cores or extensions 68 would extend from internal walls 56 of mold 52 and create voids or thinned walls in distal end 24 of respiratory tube 26. The voids could also be created by many other methods, including avoiding the introduction of the molding material onto cores 68. This could be accomplished by deliberately manipulating mold 52 during introduction of the molding material thereon. The molding material could also be introduced onto cores 68 to produce protruding members, and the protruding members could be removed therefrom after curing has taken place.

Hollow peripheral portion 40 is connected to base 42 of positioning shield 22 to form the laryngeal airway 10. Base 42 may be connected to peripheral portion 40 of the laryngeal mask prior to, or after the introduction of the molding material into mold 52. Base 42 may be connected to peripheral portion 40 by any known connection method, including but not limited to the use of heat, pressure, chemical, adhesives, or a combination of either. The specific method employed is largely dependent upon the specific composition of the laryngeal airway desired. In one embodiment, base 42 is connected to peripheral portion 40 by the application of heat. Pressure may also be used to connect base 42 and peripheral portion 40. When pressure is employed as a means for connection, force is applied to the two components, which results in fusion. Base 42 and peripheral portion 40 may also be connected using chemical adhesives. The specific type of adhesive employed would be apparent to those skilled in the art, and is largely dependent on the specific composition of the laryngeal airway desired. Another connection method involves introducing base 42 into mold 52 prior to introduction of the molding material therein. As the molding material cures about base 42, peripheral portion 40 and base 42 are fluidly connected.

In one embodiment of the invention, a secondary base is introduced onto base 42. In some cases, base 42 may be too thin to withstand the trauma associated with use. In that case, a secondary base may be introduced onto base 42 after laryngeal airway 10 is formed to add stability to base 42.

With reference to FIG. 1, base 42, and the secondary base also comprise respiratory tube 26. In this embodiment, respiratory tube 26 comprises a central unitary structure. The central unitary structure comprises a base and a respiratory tube, generally. This central unitary structure may be inserted into mold 52 prior to the introduction of the molding material therein. The central unitary structure generally comprises the same material as peripheral portion 40. However, it is envisioned that it may comprise different materials of manufacture than inflatable peripheral portion 40. The materials of manufacture need not be the same, however, they must be able to be connected. In accordance with the invention, the central unitary structure is placed into mold 52 such that the outer periphery the central unitary structure will be aligned with the inner periphery of peripheral portion 40 after curing. When the molding material is introduced and allowed to cure about internal walls 56, positioning shield 22, including peripheral portion 40, becomes fluidly connected with the central unitary structure. Alternatively, peripheral portion 40 is allowed to cure about internal walls 56, and is brought into fluid connection with the central unitary structure after peripheral portion 40 is formed. Any known connection means may be employed.

The molding material employed may generally be any medically inert flexible plastic material, rubber material, or any other material, including but not limited to polyvinyl chloride ("PVC"), polyurethane, EVA, TPE, silicone, polyether block amide, another flexible resin, combinations or mixtures thereof and the like. As such, one skilled in the art would appreciate that the molding material may be in various forms, including but not limited to paste and liquid forms. In specific embodiment of the invention, the molding material is PVC. PVC is preferred because it is in liquid form when warmed, which facilitates easy introduction into molds, is medically inert and able to cure at room temperature. It is also inexpensive, and therefore ideal for producing disposable laryngeal airways 10, which are commonly used by medical personnel. In another specific embodiment of the invention, the molding material is silicone.

In view of the above, it will be seen that all the objects and features of the present invention are achieved, and other advantageous results obtained. The description of the invention contained herein is illustrated only, and is not intended in a limiting sense.

What is claimed:

1. A method of making a laryngeal airway of the type that includes a respiratory tube and an inflatable positioning shield, the shield having a base and a hollow, peripheral portion, the respiratory tube comprising a tubular body and a proximal end lumen, and a distal end lumen formed there through, the method comprising:
   introducing at least one molding material into a mold;
   wherein the mold has a cavity defined by internal walls;
   wherein the mold has at least one core within its cavity, the core being adapted to form the proximal end lumen, tubular body and distal end lumen of the respiratory tube and the hollow, peripheral portion of the inflatable positioning shield;
   wherein the internal walls of the mold conform to external walls of the laryngeal airway; and
   allowing the molding material to cure about the internal walls of the mold and the at least one core, thereby forming the laryngeal airway in a non-inverted form.

2. The method of claim 1 wherein the molding material is a paste.

3. The method of claim 1 wherein the molding material is silicone.

4. The method of claim 1 wherein the at least one core comprises a proximal portion, a central portion, and a distal portion, the proximal portion adapted to form the proximal end lumen, the tubular body and a distal end of the respiratory tube, the central portion adapted to form the distal end lumen of the respiratory tube and the distal portion adapted to form the hollow peripheral portion of the inflatable positioning shield.

5. The method of claim 4 wherein the core comprises a handle.

6. The method of claim 4 comprising at least two cores.

7. The method of claim 1 further comprising connecting an additional respiratory tube to the proximal end of the respiratory tube.

8. The method of claim 1 wherein the molding material is a liquid.

9. The method of claim 1 comprising two cores.

10. The method of claim 1 wherein the internals walls of the mold conform to the external walls of a laryngeal mask comprising a hollow peripheral portion that has a recessed front portion.

11. The method of claim 1 wherein introducing the molding material into the mold comprises introducing the molding material into the mold using pressure.

12. The method of claim 7 wherein the connection is accomplished using heat, pressure, or an adhesive.

13. The method of claim 1 wherein introducing the molding material into the mold comprises pouring the molding material into the mold.

14. The method of claim 8 wherein the molding material is polyvinylchloride.

15. The method of claim 8 wherein the molding material is a plastic.

16. The method of claim 1 wherein the internal walls of the mold conform to the external walls of a laryngeal airway comprising an inflatable positioning shield and a respiratory tube, the inflatable positioning shield having a hollow peripheral portion in fluid communication with the base, the base having a recessed front portion, a shield recess formed after inflation of the peripheral portion, and a rear portion formed between the base and the peripheral portion after inflation of the peripheral portion, the respiratory tube having a proximal end lumen, a curved tubular body of sufficient size to permit passage of endotracheal tubes or related medical instruments therethrough, and a distal end passing through and secured to the rear portion of the positioning shield, the distal end terminating at a distal lumen, the distal lumen passing through and secured to the rear portion of the positioning shield, and wherein the at least one core is adapted to form the hollow portions of the laryngeal airway.

17. The method of claim 1 wherein the molding material is introduced into the mold in an amount that fills the cavity of the mold.

18. The method of claim 16 wherein the recessed front portion comprises a material that imparts sufficient pliability to facilitate cupping of a patients trachea after inflation of the positioning shield.

19. The method of claim 1 wherein the molding material is at least one selected from the group consisting of polyvinylchloride, silicone, polyurethane, EVA, TPE, polyether block amide, a flexible plastic, a rubber material and combinations or mixtures thereof.

20. The method of claim 1 wherein the step of introducing at least one molding material onto internal walls of a mold is repeated after the molding material is allowed to cure.

21. The method of claim 1 further comprising warming the mold prior to introducing the molding material therein.

22. The method of claim 1 further comprising cooling the mold prior to introducing the molding material therein.

23. The method of claim 1 further comprising cooling the mold after the molding material is introduced therein.

24. The method of claim 1 wherein the at least one core comprises a distal portion, the distal portion adapted to form the hollow peripheral portion of the inflatable positioning shield.

25. The method of claim 1 wherein an amount of molding material is introduced into the mold that is sufficient to form external walls of the inflatable peripheral portions of the laryngeal airway that are about 0.5 to about 1.5 millimeters thick.

26. The method of claim 1 wherein the inflatable peripheral portions of the laryngeal airway formed is about 0.5 to about 1.5 millimeters thick.

27. The method of claim 1 further comprising warming the mold after the molding material is introduced therein.

28. The method of claim 1 comprising three cores.

29. A method of making a laryngeal airway of the type that includes a respiratory tube and an inflatable positioning shield, the shield having a base and a hollow peripheral portion, the respiratory tube comprising a proximal end lumen, a tubular body of sufficient size to permit passage of endotracheal tubes or related medical instruments therethrough, a distal end, passing through and secured to the positioning shield and a distal end lumen passing though and secured to the positioning shield, the method comprising:
introducing at least one molding material into a mold;
wherein the mold has a cavity defined by internal walls;
wherein the mold has at least one core within its cavity, the core being adapted to form the respiratory tube and the hollow, peripheral portion of the positioning shield;
wherein the internal walls of the mold conform to external walls of the laryngeal airway;
wherein the at least one core comprises a proximal portion, central portion, and a distal portion, the proximal portion adapted to form the proximal end lumen, the tubular body, and the distal end of the respiratory tube, the central portion adapted to form the distal lumen of the respiratory tube and the distal portion adapted to form the hollow, peripheral portion of the inflatable positioning shield; and
allowing the molding material to cure about the internal walls of the mold and the at least one core, thereby forming the laryngeal airway in a non-inverted form.

30. A method of making a laryngeal airway of the type that includes a respiratory tube and an inflatable positioning shield, the shield having a base and a hollow peripheral portion, the respiratory tube comprising a proximal end lumen, a tubular body of sufficient size to permit passage of endotracheal tubes or related medical instruments therethrough, and a distal end secured to the positioning shield, the distal end terminating at a distal lumen, which is secured to the positioning shield, the method comprising:
introducing silicone into a mold;
wherein the mold has a cavity defined by internal walls;
wherein the mold has at least one core within its cavity, the core being adapted to form the respiratory tube and the hollow peripheral portion of the positioning shield;
wherein the internal walls of the mold conform to external walls of the laryngeal airway;
wherein the at least one core comprises a proximal portion, a central portion, and a distal portion, the proximal portion adapted to form the proximal end lumen, the tubular body, and the distal end of the respiratory tube, the central portion adapted to form the distal end lumen of the respiratory tube and the distal portion adapted to form the hollow peripheral portion of the inflatable positioning shield;
and allowing the silicone to cure about the internal walls of the mold and the at least one core, thereby forming the laryngeal airway in a non-inverted form.

31. A method of making a laryngeal airway of the type that includes an inflatable positioning shield, the shield having a base and a hollow peripheral portion, the method comprising:
introducing at least one molding material into a mold;
wherein the mold has a cavity defined by internal walls;
wherein the internal walls of the mold conform to external walls of the laryngeal airway;
wherein the mold has at least one core within its cavity, the core being adapted to form the hollow peripheral portion of the positioning shield; and
allowing the molding material to cure about the internal walls of the mold and the at least one core, thereby forming the laryngeal airway in a non-inverted form.

32. The method of claim 31 further comprising connecting a respiratory tube to the positioning shield.

33. The method of claim 31 further comprising introducing the base into the mold prior to introduction of the molding material therein.

34. The method of claim 31 wherein the base comprises a respiratory tube.

35. The method of claim 31 further comprising introducing a secondary base onto the base.

36. The method of claim 31 wherein the secondary base comprises a respiratory tube.

* * * * *